US010391251B2

(12) United States Patent
Young et al.

(10) Patent No.: US 10,391,251 B2
(45) Date of Patent: Aug. 27, 2019

(54) DRUG DELIVERY DEVICE WITH PRESSED METAL PLUNGER ROD

(71) Applicant: OVAL MEDICAL TECHNOLOGIES LIMITED, Cambridge (GB)

(72) Inventors: Matthew Young, Cambridge (GB); Ralph Lamble, Cambridge (GB)

(73) Assignee: OVAL MEDICAL TECHNOLOGIES LIMITED, Cambridge (GB)

(*) Notice: Subject to any disclaimer, the term of this patent is extended or adjusted under 35 U.S.C. 154(b) by 591 days.

(21) Appl. No.: 14/413,577

(22) PCT Filed: Jul. 9, 2013

(86) PCT No.: PCT/GB2013/051803
§ 371 (c)(1),
(2) Date: Jan. 8, 2015

(87) PCT Pub. No.: WO2014/009706
PCT Pub. Date: Jan. 16, 2014

(65) Prior Publication Data
US 2015/0174331 A1     Jun. 25, 2015

(30) Foreign Application Priority Data

Jul. 10, 2012 (GB) .................................. 1212238.8

(51) Int. Cl.
*A61M 5/315* (2006.01)
*A61M 5/20* (2006.01)
(Continued)

(52) U.S. Cl.
CPC ...... *A61M 5/31513* (2013.01); *A61M 5/2033* (2013.01); *A61M 5/288* (2013.01);
(Continued)

(58) Field of Classification Search
CPC .......... A61M 5/31511; A61M 5/31513; A61M 5/31515; A61M 5/2033; A61M 5/288;
(Continued)

(56) References Cited

U.S. PATENT DOCUMENTS 3,556,100 A * 1/1971 Hurschman ......... A61M 5/2033
604/138
3,958,570 A    5/1976 Vogelman et al.
(Continued)

FOREIGN PATENT DOCUMENTS

| EP | 0518416 A1 | 12/1992 |
|---|---|---|
| WO | 2006068650 A1 | 6/2006 |
| WO | 2012073035 | 6/2012 |

OTHER PUBLICATIONS

International Search Report from corresponding PCT application PCT/GB2013/051803, dated Dec. 13, 2013.
(Continued)

*Primary Examiner* — Nathan R Price
*Assistant Examiner* — Justin L Zamory
(74) *Attorney, Agent, or Firm* — Lando & Anastasi, LLP

(57) ABSTRACT

A pre-filled drug delivery device, comprising a housing, a drug container within the housing and containing a drug; a plunger held within the drug container, movement of the plunger within the drug container being operative to dispense the drug from the drug container through an outlet; and a drive mechanism within the housing including a stored energy source and a plunger rod held in locked position against the stored energy source prior to activation of the device, wherein on activation of the device the stored energy source moves the plunger rod such that the plunger rod moves the plunger within the housing wherein the plunger rod comprises a longitudinal shaft formed from sheet metal, wherein the sheet metal defines a plane, and wherein the sheet metal is deformed so that the longitudinal shaft com-
(Continued)

prises an out-of-plane engagement surface, the out-of-plane engagement surface configured to engage a retaining surface on the housing or on a component of the drive mechanism, to hold the plunger rod in the locked position.

18 Claims, 6 Drawing Sheets

(51) Int. Cl.
    *A61M 5/28*     (2006.01)
    *A61M 5/32*     (2006.01)
    *A61M 5/31*     (2006.01)

(52) U.S. Cl.
    CPC ....... *A61M 5/31511* (2013.01); *A61M 5/3202* (2013.01); *A61M 5/3204* (2013.01); *A61M 2005/206* (2013.01); *A61M 2005/3121* (2013.01); *A61M 2005/31518* (2013.01); *A61M 2005/31521* (2013.01)

(58) Field of Classification Search
    CPC .............. A61M 5/3202; A61M 5/3204; A61M 2005/206; A61M 2005/3121; A61M 2005/31518; A61M 2005/31521
    See application file for complete search history.

(56) References Cited

U.S. PATENT DOCUMENTS

| | | | |
|---|---|---|---|
| 7,331,934 B2 * | 2/2008 | Suresh | A61M 5/5013 604/110 |
| 2011/0251549 A1 | 10/2011 | Matusch | |
| 2014/0046259 A1 * | 2/2014 | Reber | A61M 5/2033 604/136 |

OTHER PUBLICATIONS

Search Report from corresponding GB application GB1212238.8, dated Nov. 7, 2012.
Written Opinion from corresponding PCT application PCT/GB2013/051803, dated Dec. 13, 2013.

* cited by examiner

DRUG DELIVERY DEVICE WITH PRESSED METAL PLUNGER ROD

CROSS-REFERENCE TO RELATED APPLICATIONS

This application is a U.S. National Stage Application under 35 U.S.C. § 371 of International Application No. PCT/GB2013/051803, filed Jul. 9, 2013, which is hereby incorporated herein by reference in its entirety. PCT/GB2013/051803 claims priority to Great Britain Patent Application No. 1212238.8 filed Jul. 10, 2012.

FIELD OF THE INVENTION

The invention relates to pre-filled drug containers having automatic delivery mechanisms that are kept in an energised state prior to use. In particular, the invention relates to drug containers that comprise a plunger rod that drives a plunger within a drug container to deliver a drug, in which the plunger rod is subjected to significant load by the delivery mechanism prior to drug delivery.

BACKGROUND TO THE INVENTION

Prefilled drug containers allowing for self administration of drugs are becoming increasingly prevalent, as self administration has clear benefits in terms of cost to health care providers as well as improving patient convenience.

One type of prefilled drug container is an autoinjector, which includes an automatic delivery mechanism which, once activated, provides for automatic delivery of the drug and sometimes also automatic needle insertion. In autoinjectors, the delivery mechanism includes a stored energy source which, when released, drives the drug delivery mechanism and optionally the needle insertion. The stored energy source acts on a drive member, such as a plunger rod, which engages a plunger within the drug container, and drives the plunger within the drug container. In many autoinjector designs, the same plunger rod also drives the drug container through the autoinjector housing to perform a needle insertion operation.

Prior to use, the stored energy source must be retained in an energised condition. The plunger rod can be used to retain the stored energy source by engagement of the plunger rod with a retaining element on or coupled to the housing of the device. The plunger rod is then loaded between the stored energy source, typically a compressed spring, and the retaining element and is held in this condition for an indefinite period between assembly of the device and use of the device.

Typically autoinjector mechanisms are manufactured using plastic components when possible because of the ability to accurately mould small mechanical components out of plastics materials at low cost. However, a problem with plastics components, particularly for drug delivery devices containing drugs with a long shelf life, is that plastics materials tend to creep and have relatively low tensile and compressive strength compared to some metals and other materials. A drive member which is loaded by the force of a compressed spring may deform or even break over time, such that the proper functioning of the autoinjector is impaired or prevented.

The plunger rod is generally required to have a small cross-section along at least part of its shaft length, because it may need to fit inside the drug container or the energy source such as a spring). This limits the strength of the shaft, and exacerbates the risk of deformation or breakage described above, particularly if the shaft is made of plastic.

Clearly a metal shaft has advantages, but the cost of a metal plunger rod can potentially be much higher than a plastic one, particularly if sophisticated manufacturing processes such as milling and turning are used. In order to minimise cost some autoinjector manufacturers have used flat blanked plates of metal, profiled so that their edges provide operational surfaces for instance to engage with mechanisms to retain the stored energy source and enable it to be released when appropriate. The disadvantage of this approach is that typically the edge of such a pressed plate can have burrs and sharp edges which have poor friction characteristics and can cause the performance of the aforesaid mechanisms to vary unacceptably.

It is an object of the present invention to address this problem

SUMMARY OF THE INVENTION

The invention is defined in the appended independent claims, to which reference should be made. Optional features are set out in the dependent claims.

In a first aspect, the invention provides a pre-filled drug delivery device, comprising
 a housing;
 a drug container within the housing and containing a drug;
 a plunger held within the drug container, movement of the plunger within the drug container being operative to dispense the drug from the drug container through an outlet; and
 a drive mechanism within the housing including a stored energy source and a plunger rod held in locked position against the stored energy source prior to activation of the device, wherein on activation of the device the stored energy source moves the plunger rod such that the plunger rod moves the plunger within the housing;
 wherein the plunger rod comprises a longitudinal shaft formed from sheet metal, wherein the sheet metal defines a plane, and wherein the sheet metal is deformed so that the longitudinal shaft comprises an out-of-plane engagement surface, the out-of-plane engagement surface configured to engage a retaining surface on the housing or on a component of the drive mechanism, to hold the plunger rod in the locked position.

"Out-of-plane" in this context is relative to the plane defined by the surface of the sheet metal of the shaft prior to deforming the sheet metal. Sheet metal is metal that has been rolled or formed into a sheet having a flat surface defining a plane and having a thickness or gauge between a foil and a plate. So the formation of the out-of-plane engagement surface means that that each of the largest surfaces of the shaft do not lie in a single plane The use of deformed or bent sheet metal to form the shaft of the plunger rod provides a plunger rod that does not creep significantly and provides a reliable locking engagement to retain the stored energy source, while being inexpensive and easy to manufacture in high volumes. The sheet metal can be bent or deformed to provide any desired shape without adding significant expense to the process.

Advantageously, the shaft is formed by blanking a sheet of metal. Blanking is an inexpensive and reliable process for forming a high volume of components. The blanked sheet metal shaft may be deformed into a desired shape by a pressing tool. The deforming operation may be performed before or simultaneously with blanking or cutting the shaft from a sheet of metal, or may be performed subsequent to a blanking operation.

The plunger rod must be able to withstand the load exerted by the stored energy source, which is typically a spring but may be another energy source such as pressurised gas, and must not significantly deform or creep over time. It may be many months between assembly or otherwise loading if reusable) of the drug delivery device, and activation of the device and during that that time the plunger rod will be under tension or compression, depending on the configuration of the device. If the plunger rod is under tension, i.e. is being stretched, under the load exerted by the stored energy source, the plunger rod will get longer over time. If the plunger rod is being compressed it will get shorter over time. With plastics material this change in length can become so significant that it prevents the device from operating correctly. For example, in an autoinjector, if the plunger rod is too long it may prevent a needle safety mechanism deploying after the drug has been delivered or it may damage a sterile seal within the device prior to activation. A plunger rod formed from steel or brass for example, will not creep to the same extent and may be made sufficiently thin that it is flexible enough to form part of a release mechanism for activating the device.

The shaft may be made from very thin sheet metal, i.e. low gauge, without affecting the reliability of the engagement surface. The deformation of the sheet metal to form the engagement surface means that it can be formed to have as large a surface area as needed to ensure a reliable locking engagement. In contrast, using the edge of a flat blanked metal plate to form an engagement surface means that the thickness of the metal determines the extent of the engagement surface.

The shaft may be formed from sheet metal with a thickness of 0.5 mm or less to provide the desired flexibility, and may be formed from spring steel. Other metals and alloys, including other types of steel, brass, bronze alloys, copper alloys and aluminium alloys may alternatively be used.

When the device is activated the plunger rod must be reliably released so that it can be driven to eject the drug. If a blanking process is used to cut the plunger rod shafts from a sheet, burrs are typically formed on the edges of the shaft on the side of the sheet opposite to the initial position of the blanking tool. These burrs form a jagged edge that, if placed into contact with a plastic surface on the housing or drive mechanism, can become embedded in that surface. This, in turn, may prevent the release of the plunger rod from the locking surface when required rendering the autoinjector unreliable. However, by forming the shaft by deforming a planar i.e. flat) sheet metal component, an out-of-plane engagement surface can be formed on the side of the sheet without any burrs, i.e. the side of the sheet metal which the blanking tool first contacts during the stamping operation. The opposite surface, which is likely to have some burred edges, can be faced away from the retaining surface.

The shaft may be deformed to provide more than one out-of-plane engagement surface.

In use, the shaft member or members may flex to allow the out-of-plane engagement surface or surfaces to disengage from the retaining surface or surfaces after the device has been activated. The shaft members may be prevented from flexing prior to activation by one or more retaining elements that engage the shaft members. The retaining element or elements may engage an opposite side of the shaft to the out-of-plane engagement surface, but may be sized so that they do not contact the edges of the shaft that may have burrs.

The plunger rod may comprise a plunger engagement surface for engagement with the plunger and the longitudinal shaft may extend rearward from the plunger engagement surface. In one advantageous embodiment, the shaft comprises two shaft members extending rearward from the plunger engagement surface. The two shaft members may be formed from a single pressed metal element.

The plunger rod may further comprise a plunger engagement element fixed to the shaft, the plunger engagement element comprising at least a part of the plunger engagement surface. The plunger engagement element may include piercing features formed on a front end and configured to pierce a seal on the drug container following activation of the device.

The plunger engagement element may be formed from a plastics material. The plunger engagement element may be moulded around the shaft. Alternatively the shaft may be assembled to the plunger engagement element using a mechanical engagement.

In another aspect of the invention, there is provided a method of manufacturing a pre-filled drug delivery device, the drug delivery device comprising: a housing, a drug container containing within the housing and containing a drug; a plunger held within the drug container, movement of the plunger within the drug container being operative to dispense the drug from the drug container; and a drive mechanism within the housing and including a stored energy source and a plunger rod, the plunger rod held in a locked position against the stored energy source prior to activation of the device, wherein on activation of the device the stored energy source moves the plunger rod and the plunger rod moves the plunger within the housing, wherein the plunger rod comprises a longitudinal shaft, the method comprising the step of:

forming the longitudinal shaft from sheet metal, wherein the sheet metal defines a plane, and deforming the sheet metal so that the longitudinal shaft comprises an out-of plane engagement surface, the out-of-plane engagement surface configured to engage a retaining surface on the housing or on a component of the drive mechanism. The step of forming the longitudinal shaft may comprise blanking the shaft from the sheet metal.

BRIEF DESCRIPTION OF THE DRAWINGS

Embodiments of the present invention will now be described in detail by way of example only, with reference to the accompanying drawings, in which.

DETAILED DESCRIPTION

Figure 1:
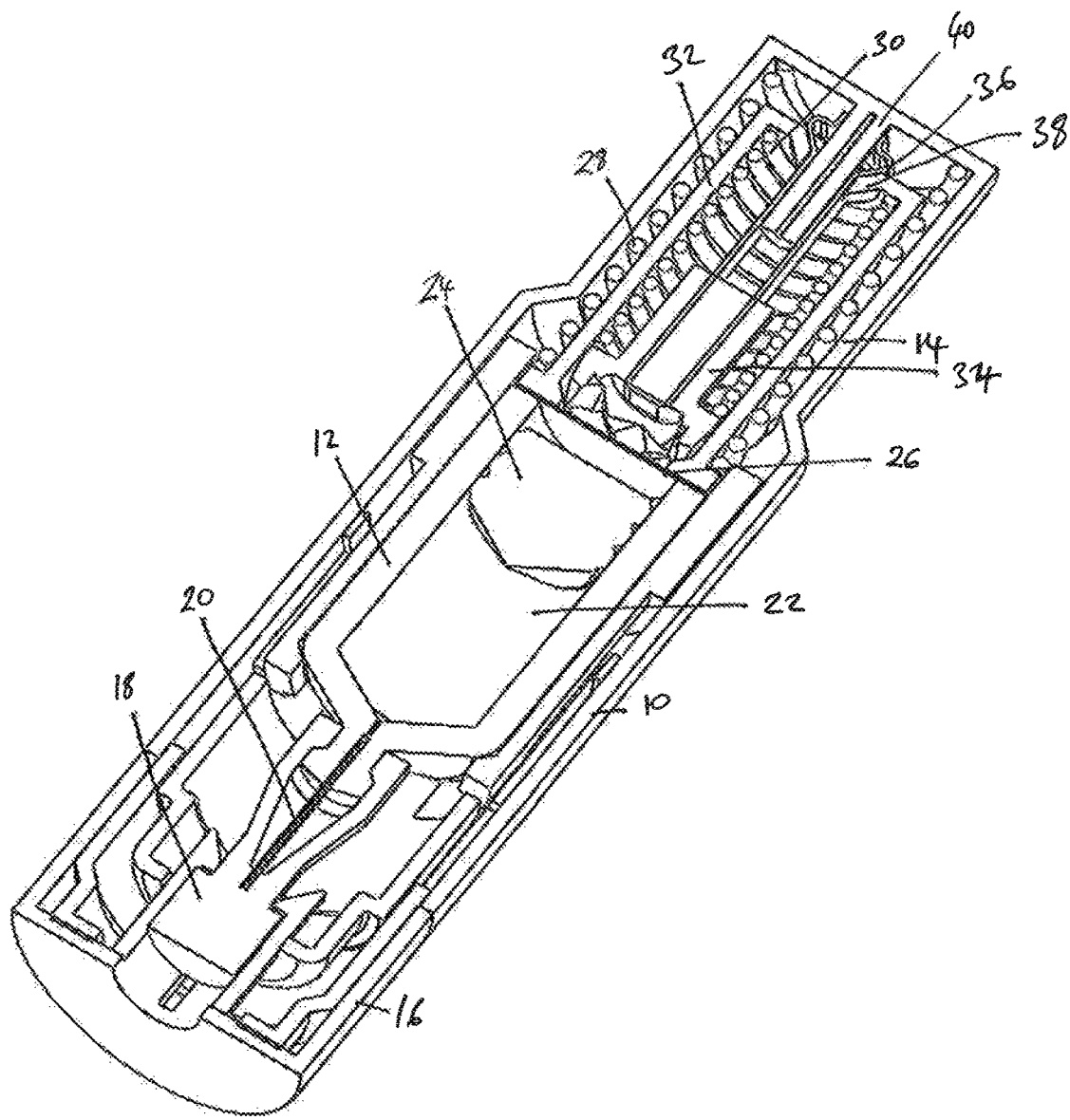
FIG. 1 is a cross section through an autoinjector in accordance with one embodiment of the invention.

FIG. 1 is a cross section of an autoinjector in accordance with one embodiment of the invention. The autoinjector comprises an outer housing 10, a drug container 12 within the outer housing 10, a drive mechanism 14 positioned within the housing 10, rearward of the drug container 12, a cap 16 coupled to the housing 10 and a needle shield connected to the cap 16. The needle shield is also coupled to the drug container 12 and maintains a needle 20 in a sterile condition prior to use. A drug 22 is held within the drug container and is positioned between the front end of the container 12 to which the needle 20 is fixed and a plunger 24 which closes a rear end of the drug container. A seal 26 is provided behind the plunger 24 to provide a sterile seal to ensure that the drug is maintained in a pristine condition prior to use.

In the embodiment shown in FIG. 1, the drive mechanism comprises two drive springs 28, 30. The first drive spring 28 is configured to drive the drug container 12 through the housing 10 to a needle insertion position, in which the needle 20 extends beyond the housing and, in use, into the body of a patient. Following needle insertion, the second spring 30 is used to drive the plunger 24 through the drug container 12 to dispense the drug 22 through the needle 20 and into the patient. Accordingly, the drive mechanism 14 is configured to release a first spring 28 upon activation of the device and, once the drug container has reached or is close to a needle insertion position, release the second spring 30 to dispense the drug.

The first spring 28 acts upon an outer drive member 32 which abuts the rear end of the drug container 12 so that extension of the spring 28 drives the outer drive member forwardly, thereby pushing the drug container 12 through the housing 10. The inner drive spring 30 is retained in a compressed condition during a needle insertion operation between plunger rod 34 and outer drive member 32. Plunger rod 34 is prevented from moving forwardly relative to outer drive member 32 by the engagement of lugs 36 on the plunger rod with retaining surfaces 38 on the outer drive member 32. It is only when outer drive member 32 has travelled forward to a position in which engagement member 40 is no longer engaged with the plunger rod 34 that the plunger rod 34 can flex to disengage lugs 36 from the outer drive member 32 and thereby move forward to drive the plunger 24 through the drug container.

In the embodiment shown in FIG. 1, the plunger rod is held in tension by the retaining surfaces 38, against the action of the inner drive spring 30, until it is released. However, it should be clear that the specific drive mechanism 14 shown in FIG. 1 is an example only and that the plunger rod 32 may be used in other delivery mechanisms, for example a mechanism in which the plunger rod is compressed by the stored energy source prior to activation.

Figure 2:
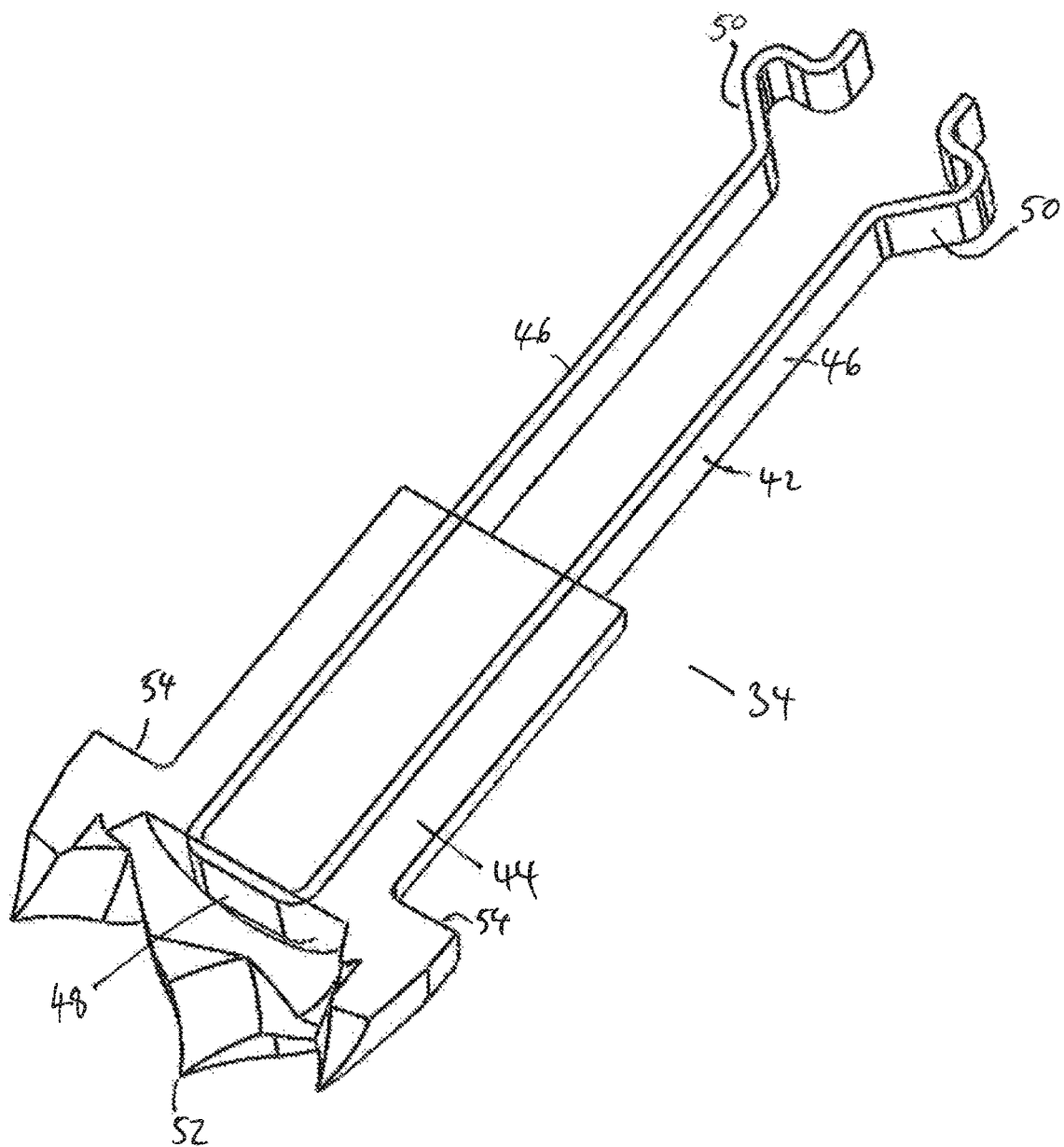
FIG. 2 is a cross section through the plunger rod of the autoinjector of FIG. 1.

FIG. 2 is a cross section of the plunger rod of FIG. 1. The plunger rod 34 is formed from a sheet metal shaft 42 and a plastic, plunger engagement member 44. The sheet metal shaft 42 is formed from a single piece of sheet spring steel that has been pressed to the desired shape. The shaft 42 is substantially U shaped having two, substantially parallel shaft members 46. Each of the shaft members 46 extends longitudinally away from a front, plunger engagement surface 48 and includes an out-of-plane engagement surface 50 on a lug 36 which allows the plunger rod to engage with the retaining surfaces 38 on the outer drive member. "Out-of-plane" in this context is relative to the plane defined by the surface of the sheet metal of the shaft prior to deformation of the sheet. In other words, the formation of an out-of-plane engagement surface means that that each of the largest faces of the shaft do not lie in a single plane.

The plunger engagement member is moulded around the shaft 42, and in this example is formed from polypropylene. Creep of a plastic plunger engagement member is not a significant problem if formed with sufficient thickness for a given width. However it should be clear that the plunger engagement member can be formed from any suitable material, including metal. Indeed the plunger engagement member is not an essential feature of the plunger rod as the forwardly facing surface of the shaft 42 may be used to engage the plunger and may be shaped to provide a suitable seating surface for a spring or other stored energy source, as well as any required piercing elements.

It can be seen that the plunger engagement member extends only partially along the length of the shaft 42 this ensures that the rearward portion of the shaft 42 is able to flex sufficiently to allow the out-of-plane engagement surfaces 50 to disengage from the retaining surfaces 38.

The plunger engagement member includes an annular, rearward facing surface 54 on which the inner drive spring 30 is seated. The plunger engagement member also includes a number of piercing features 52 at its front end. These piercing features are operable to rupture the sealing element 26 on the rear of the drug container immediately prior to engagement of the plunger rod with the plunger 24.

Figure 3:
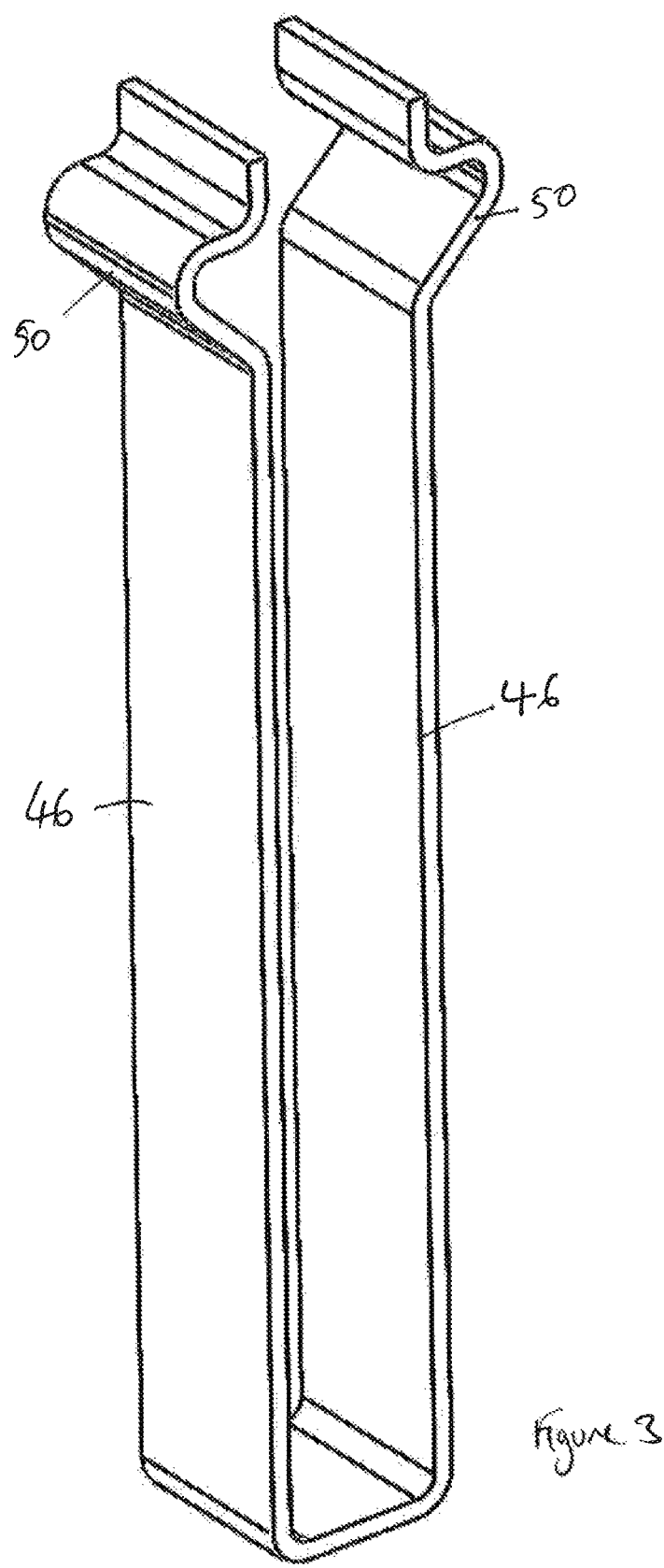
FIG. 3 is a perspective view of the pressed metal shaft of the plunger rod of FIG. 2.

FIG. 3 is a perspective view of the metal shaft 42 alone. It can be clearly seen in FIG. 3 that the shaft is formed from a single metal component pressed to the desired shape. The out-of-plane engagement surfaces 50 can be formed in any desired configuration, and although the shaft members 46 are substantially parallel in the embodiment shown in FIGS. 1 to 3, they may be formed to diverge or converge from one another.

In a metal blanking operation, the edges of the blanked component on the surface of the metal opposite to the side from which the blanking tool contacts the metal sheet, typically have burrs formed on them. This is an inevitable consequence of the blanking operation. These burrs can be removed by abrasion but that adds considerable expense. In the embodiments shown in FIGS. 1 to 4 and in FIGS. 5 to 6, the shaft is generally U shaped and is pressed or bent such that the edges that are likely to have burrs face inwardly and do not form part of the surfaces 50 that contact the outer drive member 32. Any burrs or jagged edges on the out-of-plane engagement surfaces 50 that engage the outer drive member 32 might result in failure of the piston rod to disengage from the outer drive member and thereby interfere with proper operation of the device. An advantage of the deformed metal design of the piston rod in accordance with the embodiments described is that the burred edges of the metal can be kept away from the retaining surfaces 38.

Figure 4:
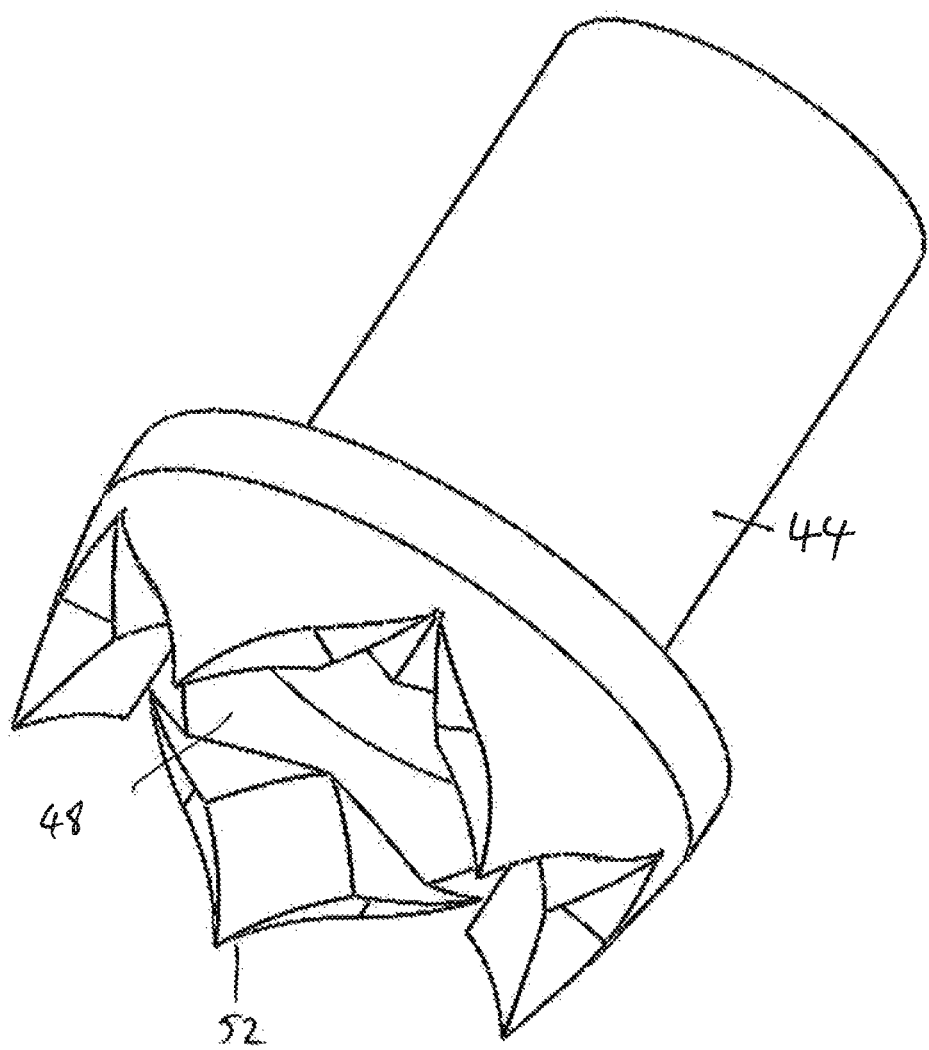
FIG. 4 is a perspective view of the plunger engagement member of FIG. 2.

FIG. 4 is a perspective view of the plunger engagement member alone which more clearly illustrates the arrangement of piercing features 52 circumferentially spaced around the front face of the plunger engagement member.

In the examples shown in FIGS. 1, 2 and 3, a portion of the metal shaft 42 forms a portion of the plunger engagement surface 48. However it should be clear that this is optional and that the metal shaft 42 may be embedded within the plunger engagement member to a greater or lesser degree as desired.

Figure 5:
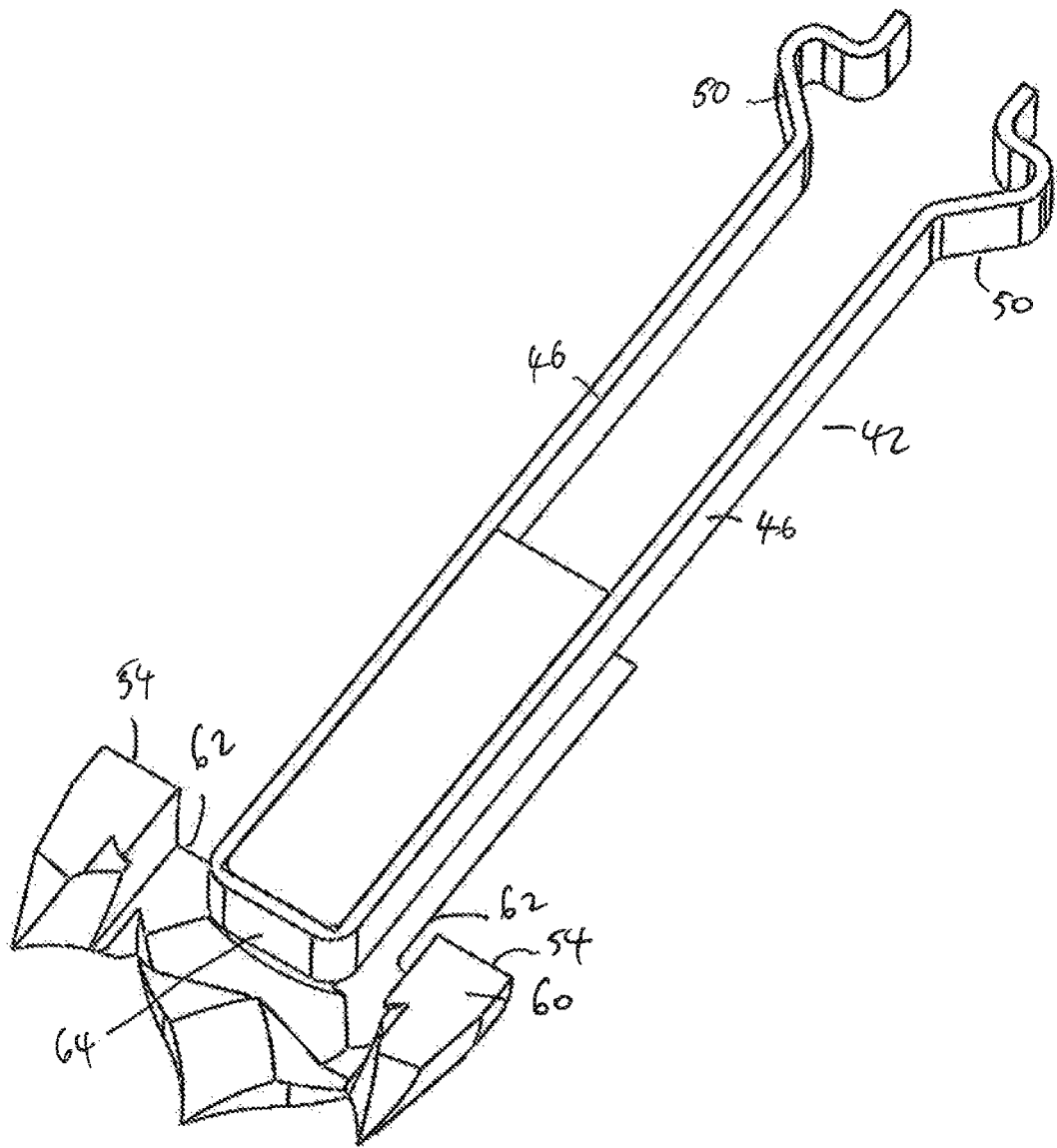
FIG. 5 shows a plunger rod for use in a drug delivery device in accordance with another embodiment of the invention.
Figure 6:
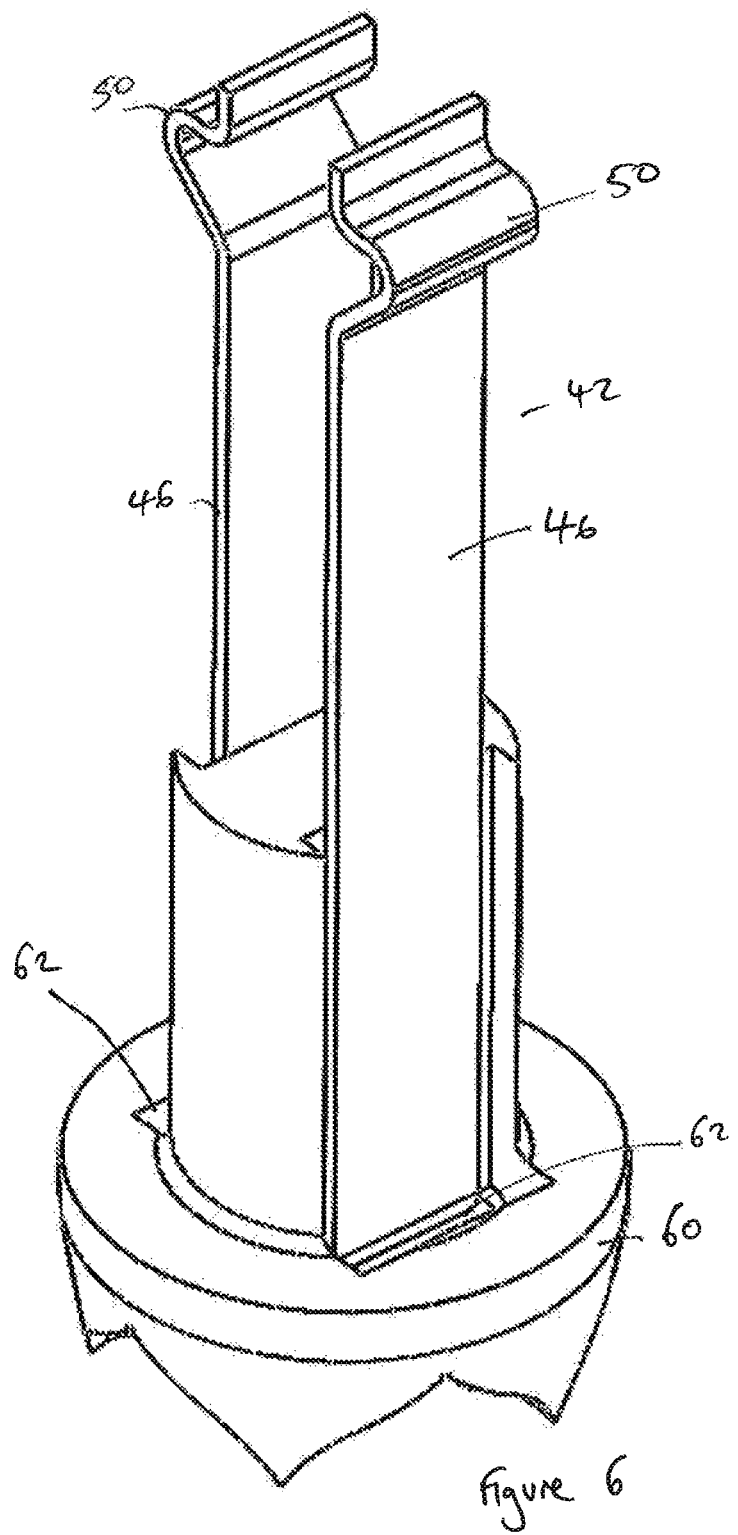
FIG. 6 is a perspective view of the plunger rod of FIG. 6

FIG. 5 illustrates an alternative embodiment of a plunger in accordance with the invention. In the embodiment of FIG. 5 the metal shaft 42 mechanically assembled to the plunger engagement member 60 rather than the plunger engagement member being moulded around it. The metal shaft in the embodiment of FIGS. 5 and 6 is substantially the same as the metal shaft of the embodiment of FIG. 3 and accordingly identical reference numerals have been used to refer to it. However the plunger engagement member 60 is different to the plunger engagement member of the embodiment of FIGS. 1 to 4. In the embodiment of FIG. 5 the plunger engagement member 60 is moulded from a plastics material, such as polypropylene although any suitable material, including metal may be used) and includes a pair of slots 62. The shaft members 46 can be passed through the slots from the front end until a lateral portion of the shaft 64 engages with the plunger engagement member 60. No further fixing is required between the plunger engagement member and the shaft as the shaft is held in tension prior to use, and during use the plunger engagement member is directly driven by the inner spring 32. However, the metal shaft may be shaped to provide a mechanical retaining engagement with the plunger engagement member 60, relying on the resilient nature of the metal shaft 42.

The embodiments described all relate to a particular autoinjector design shown in FIG. 1, However, the invention can clearly be applied to other autoinjector designs and indeed to other drug delivery devices having a plunger rod retaining a stored energy source prior to use.

The invention claimed is:

1. A pre-filled drug delivery device, comprising:
   a housing;
   a drug container within the housing and containing a drug;
   a seal on the drug container;
   a plunger held within the drug container, movement of the plunger within the drug container being operative to dispense the drug from the drug container through an outlet; and
   a drive mechanism within the housing including a stored energy source and a plunger rod held in a locked position against the stored energy source prior to activation of the device, wherein on activation of the device the stored energy source moves the plunger rod such that the plunger rod moves the plunger within the housing,
   wherein the plunger rod includes a longitudinal shaft formed from sheet metal, wherein the sheet metal defines a plane, and wherein the sheet metal is deformed so that the longitudinal shaft has an out-of-plane engagement surface, the out-of-plane engagement surface configured to engage a retaining surface on the housing or on a component of the drive mechanism, to hold the plunger rod in the locked position,
   wherein the plunger rod includes a plunger engagement element fixed to the longitudinal shaft, the plunger engagement element forming at least a part of a plunger engagement surface, and the plunger engagement element includes piercing features configured to pierce the seal on the drug container following activation of the device.

2. The pre-filled drug delivery device according to claim 1, wherein the longitudinal shaft is formed by blanking a sheet of metal.

3. The pre-filled drug delivery device according to claim 2, wherein the out-of plane engagement surface has burrs which face away from the retaining surface.

4. The pre-filled drug delivery device according to claim 1, wherein the sheet metal has a thickness of 0.5 mm or less.

5. The pre-filled drug delivery device according to claim 1, comprising a plurality of out-of-plane engagement surfaces.

6. The pre-filled drug delivery device according to claim 1, wherein the longitudinal shaft extends rearward from the plunger engagement surface.

7. The pre-filled drug delivery device according to claim 6, wherein the longitudinal shaft comprises two shaft members extending rearward from the plunger engagement surface.

8. The pre-filled drug delivery device according to claim 7, wherein the two shaft members are formed from a single deformed metal element.

9. The pre-filled drug delivery device according to claim 1, wherein the plunger engagement element is formed from a plastics material and is moulded around the longitudinal shaft.

10. The pre-filled drug delivery device according to claim 1, wherein the longitudinal shaft is formed from sheet steel.

11. The pre-filled drug delivery device according to claim 1, wherein the drug delivery device is an autoinjector.

12. A method of manufacturing a pre-filled drug delivery device, the drug delivery device comprising: a housing, a drug container within the housing and containing a drug; a seal on the drug container, a plunger held within the drug container, movement of the plunger within the drug container being operative to dispense the drug from the drug container; and a drive mechanism within the housing and including a stored energy source and a plunger rod, the plunger rod held in a locked position against the stored energy source prior to activation of the device, wherein on activation of the device the stored energy source moves the plunger rod and the plunger rod moves the plunger within the housing, wherein the plunger rod comprises a longitudinal shaft, and wherein the plunger rod includes a plunger engagement element fixed to the longitudinal shaft, the plunger engagement element forming at least a part of a plunger engagement surface, and the plunger engagement element includes piercing features configured to pierce the seal on the drug container following activation of the device, the method comprising the step of:
   forming the longitudinal shaft from sheet metal, wherein the sheet metal defines a plane, and deforming the sheet metal so that the longitudinal shaft comprises an out-of-plane engagement surface, the out-of-plane engagement surface configured to engage a retaining surface on the housing or on a component of the drive mechanism, to hold the plunger rod in the locked position.

13. The method according to claim 12, wherein the step of forming the longitudinal shaft comprises blanking the longitudinal shaft from the sheet metal.

14. The pre-filled drug delivery device according to claim 10, wherein the plunger engagement surface is formed from a plastics material.

15. An autoinjector comprising:
   a housing;
   a drug container within the housing and containing a drug;
   a seal on the drug container;
   a plunger held within the drug container, movement of the plunger within the drug container being operative to dispense the drug from the drug container through an outlet; and
   a drive mechanism within the housing including a stored energy source and a plunger rod held in a locked position against the stored energy source prior to activation of the autoinjector, wherein on activation of the autoinjector the stored energy source moves the plunger rod such that the plunger rod moves the plunger within the housing;
   wherein the plunger rod includes a longitudinal shaft formed from sheet metal, wherein the sheet metal defines a plane, and wherein the sheet metal is deformed so that the longitudinal shaft comprises an out-of-plane engagement surface, the out-of-plane engagement surface configured to engage a retaining surface on the housing or on a component of the drive mechanism, to hold the plunger rod in the locked position, wherein the plunger rod includes a plunger engagement surface for engagement with the plunger and the longitudinal shaft extends rearward from the plunger engagement surface and wherein the plunger rod includes a plunger engagement element fixed to the longitudinal shaft, the plunger engagement element forming at least part of the plunger engagement surface, and wherein and the plunger engagement element includes piercing features configured to pierce the seal on the drug container following activation of the autoinjector.

16. A pre-filled drug delivery device, comprising:
a housing;
a drug container within the housing and containing a drug;
a seal on the drug container;
a plunger held within the drug container, movement of the plunger within the drug container being operative to dispense the drug from the drug container through an outlet;
an outer drive member abutting a rear end of the drug container; and
a drive spring capable of being retained in a compressed condition between the outer drive member and a plunger rod,
the plunger rod including a longitudinal shaft formed from sheet metal, the longitudinal shaft including a first arm that lies along a first plane and a second arm that lies along a second plane, each of the first and second arms including an out-of-plane engagement surface that is configured to engage a retaining surface on the housing or on the outer drive member to prevent movement of the plunger rod relative to the outer drive member and to retain the drive spring in the compressed condition, wherein the plunger rod includes a plunger engagement element fixed to the longitudinal shaft, the plunger engagement element forming at least a part of a plunger engagement surface, and the plunger engagement element including piercing features configured to pierce the seal on the drug container following activation of the device.

17. The method of claim 12, wherein the step of forming the longitudinal shaft includes forming burrs on the out-of plane engagement surface so the burrs face away from the retaining surface.

18. A method of manufacturing a pre-filled drug delivery device, the drug delivery device comprising: a housing, a drug container within the housing and containing a drug; a plunger held within the drug container, movement of the plunger within the drug container being operative to dispense the drug from the drug container; and a drive mechanism within the housing and including a stored energy source and a plunger rod, the plunger rod held in a locked position against the stored energy source prior to activation of the device, wherein on activation of the device the stored energy source moves the plunger rod and the plunger rod moves the plunger within the housing, wherein the plunger rod comprises a longitudinal shaft, the method comprising the step of:

forming the longitudinal shaft from sheet metal, wherein the sheet metal defines a plane, and deforming the sheet metal so that the longitudinal shaft comprises an out-of plane engagement surface, the out-of-plane engagement surface configured to engage a retaining surface on the housing or on a component of the drive mechanism, wherein the step of forming the longitudinal shaft includes forming burrs on the out-of plane engagement surface so the burrs face away from the retaining surface.

* * * * *